United States Patent [19]

Atkins

[11] Patent Number: 5,629,459
[45] Date of Patent: May 13, 1997

[54] OLEFIN HYDRATION PROCESS

[75] Inventor: Martin P. Atkins, Middlesex, United Kingdom

[73] Assignee: BP Chemicals Limited, London, England

[21] Appl. No.: 556,409

[22] Filed: Nov. 13, 1995

[30] Foreign Application Priority Data

Nov. 23, 1994 [GB] United Kingdom ............... 9423648

[51] Int. Cl.$^6$ .................. C07C 29/04; C07C 31/08; C07C 31/10
[52] U.S. Cl. ........................................... 568/896
[58] Field of Search ............................. 568/896

[56] References Cited

U.S. PATENT DOCUMENTS

| | | |
|---|---|---|
| 2,173,187 | 9/1939 | Tanner . |
| 3,704,329 | 11/1972 | Rindtorff et al. ............ 568/896 |

FOREIGN PATENT DOCUMENTS

| | | |
|---|---|---|
| 0031687 | 7/1981 | European Pat. Off. . |
| 0083970 | 7/1983 | European Pat. Off. . |
| 0210793 | 2/1987 | European Pat. Off. . |
| 0578441 | 1/1994 | European Pat. Off. . |
| 1069583 | 11/1959 | Germany . |
| 1156772 | 11/1963 | Germany . |
| 1193929 | 6/1965 | Germany . |
| 130935 | 8/1982 | Japan ............................... 568/896 |
| 1281120 | 7/1972 | United Kingdom . |

OTHER PUBLICATIONS

Derwent Abstract of JP A 58 181 758 dated Oct. 24, 1983.

*Primary Examiner*—Joseph E. Evans
*Attorney, Agent, or Firm*—Brooks Haidt Haffner & Delahunty

[57] ABSTRACT

This invention relates to a process for hydrating olefins to the corresponding alcohols in the vapor phase in the presence of a catalyst system comprising a heteropolyacid catalyst supported on a clay support, the clay support being a hot acid treated clay. The hot acid treated clay is prepared by progressively leaching a commercial bentonite type clay with hot acid to enable the cations in the clay to be exchanged for hydrogen ions leading to a clay support of surface area greater than 50 m$^2$/g. By using the specific acid treated clays as support, it is possible not only to increase the space-time-yield of the process but also to prolong the life of the support thereby reducing the frequency with which the support is changed or replaced on a plant.

20 Claims, No Drawings

OLEFIN HYDRATION PROCESS

The present invention relates to a process for the hydration of olefins using a catalyst system comprising heteropolyacid catalyst supported on a hot acid treated clay.

Hydration of olefins such as ethylene or propylene to the corresponding alcohols by hydration thereof in the vapour phase using a phosphoric acid catalyst deposited on a siliceous support is well known. Numerous prior art publications described such a procedure including those disclosed in GB-A-1570650, U.S. Pat. No. 4,808,559, GB-A-1371905, U.S. Pat. No. 4,038,211, U.S. Pat. No. 4,012,452, GB-A-1476534, GB-A-1306141, U.S. Pat. No. 3,996,338 and CAN-A-844004. In each of these prior publications, the nature of the siliceous support used is defined by various parameters including the pore volume, the surface area, the crush strength and the purity of the support. However, none of these documents identify the precise combination of the support and a heteropolyacid catalyst for this purpose.

Some of the prior art publications such as eg GB-A-1281120 describe a liquid phase process for the hydration of olefins using a heteropolyacid catalyst. Furthermore, U.S. Pat. No. 2,173,187 describes a process for the hydration of olefins in the vapour phase to the corresponding alcohols by using as catalyst heteropolyacid, the complex anion of which includes one element from group VI, sub-group A of the Periodic table. It is stated in this reference that the catalyst can be used with or without a support. The supports, when used, are said to be preferably silica gel although other siliceous supports such as silicic acid, Japanese acid clay, bentonite, kieselguhr, or asbestos are also listed. However, there is no disclosure of the use of hot acid treated clays (hereafter "HAT clays") as supports for the heteropolyacid catalyst.

It has now been found that by carefully controlling the aspects referred to above and especially by using HAT clays, it is possible to improve the performance of the heteropolyacid catalyst system.

Accordingly, the present invention is a process for hydrating olefins to the corresponding alcohols in the vapour phase in the presence of a catalyst system comprising a heteropolyacid catalyst supported on a clay support characterised in that the clay support is a hot acid treated clay.

The process is suitably carried out using the following reaction conditions:
a. the mole ratio of water to olefin passing through the reactor is suitably in the range from 0.1–3.0, preferably 0.1–1.0
b. the gas hourly space velocity (GHSV) of the water/olefin mixture is suitably from 0.010 to 0.25 g/min/cm$^3$ of the catalyst system, preferably from 0.03–0.10 g/min/cm$^3$ of the catalyst system.
c. the heteropolyacid catalyst concentration is from 5 to 40% w/w based on the total weight of the catalyst system, preferably from 10–30% w/w of the total weight of the catalyst system.

By the expression "hot acid treated clay" (hereafter HAT clay) as used herein and throughout the specification is meant clays which are either layered clays or pillared clays in which the clay is free from extraneous acid or other cations but may have pillars in between said layers of one or more oxides such as those of alumina, gallia, zirconia, iron oxide and chromia. Clays, especially smectite clays, are aluminosilicates with a lamellar structure and can be swollen by addition of a polar medium such as eg water, alcohols or amines which cause separation of the layers. The layers remain separated in the polar medium but upon removal of said medium eg on drying, the swollen structure collapses and shrinks back to the original size prior to contact with the polar medium. This shrinkage is arrested by a technique involving the use of the so called "pillars" to keep the layers apart. Examples of such pillars include one or more oxides of aluminium, gallium, silicon and zirconium which may be used as such or in combination with other oxides such as eg the rare earth oxides, especially cerium oxide. The pillars are usually held in place by electrostatic attraction, and are often of small length giving overall small pores. For instance, dimethylamino propyl trimethoxysilane can be used as a precursor for a silica pillar and this precursor, under aqueous acid conditions, hydrolyses producing a complex silica cation which is held in the clay by electrostatic attraction. The clay thus treated is usually then calcined to give a pillared clay which may be hydrothermally unstable. Such pillared clays, preparation thereof and the uses thereof as catalysts are reviewed by Figueras, F in Catalysis Review—Science & Engineering, Vol. 30, No. 3, 457–499 (1988).

The HAT clay is suitably prepared by progressively leaching a commercial bentonite type clay such as eg montmorillonite or a pillared clay with hot acid which enables the cations such as sodium or calcium in the clay to be exchanged for hydrogen ions leading to a clay support of an average surface area greater than 50 m$^2$/g.

Examples of this type of clay include the K10 clays which are produced by treatment of standard layered clays such as bentonite with hot acid which process depletes the clay of metals present in the untreated clay and suitably has a surface area of about 150 m$^2$/g. This acid treatment process may destroy the layered structure of the clay. The HAT clays are suitably shaped into the form of pellets or beads or globular shape by pelletisation or extrusion. Such a process is suitably carried out by the process described in published U.S. Pat. No. 5,086,031 (see especially the Examples) and is incorporated herein by reference. The shaped HAT clays suitably have an average particle diameter of 2 to 10 mm, preferably 4 to 6 mm. The HAT clay suitably has an average pore volume in the range from 0.3–1.2 ml/g, preferably from 0.6–1.0 ml/g. The support suitably has an average crush strength of at least 2 Kg force, suitably at least 5 Kg force, preferably at least 6 Kg and more preferably at least 7 Kg. The crush strengths quoted are based on average of that determined for each set of 50 beads/globules on a CHATTILLON tester which measures the minimum force necessary to crush a particle between parallel plates. The bulk density of the support is suitably at least 380 g/l, preferably at least 440 g/l.

The HAT clay support suitably has an average pore radius (prior to use) of 10 to 1000 Angstroms, preferably an average pore radius of 30 to 600 Angstroms.

In order to achieve optimum performance, the HAT clay support is suitably free of extraneous metals or elements which might adversely affect the catalytic activity of the system. The HAT clay support suitably has at least 99% w/w purity with respect to the aluminosilicate content thereof, ie the impurities which adversely affect the catalytic activity of the system are less than 1% w/w, preferably less than 0.60% w/w and more preferably less than 0.30% w/w.

The term "heteropolyacids" as used herein and throughout the specification is meant to include the free acids and salts thereof. The heteropolyacids used to prepare the olefin hydration catalysts of the present invention therefore include the free acids and the coordination-type salts thereof in which the anion is a complex, high molecular weight entity. Typically, the anion is comprises 2–18 oxygen-linked polyvalent metal atoms, which are called peripheral atoms.

These peripheral atoms surround one or more central atoms in a symmetrical manner. The peripheral atoms are usually one or more of molybdenum, tungsten, vanadium, niobium, tantalum and other metals. The central atoms are usually silicon or phosphorus but can comprise any one of a large variety of atoms from Groups I–VIII in the Periodic Table of elements. These include, for instance, lithium ions; cupric ions; divalent beryllium, zinc, cobalt or nickel ions; trivalent boron, aluminium, gallium, iron, cerium, arsenic, antimony, phosphorus, bismuth, chromium or rhodium ions; tetravalent silicon, germanlure, tin, titanium, zirconlure, vanadium, sulphur, tellurium, manganese nickel, platinum, thorium, hafnium, cerium ions and other rare earth ions; pentavalent phosphorus, arsenic, vanadium, antimony ions; hexavalent tellurium ions; and heptavalent iodine ions. Such heteropolyacids are also known as "polyoxoanions", "polyoxometallates" or "metal oxide clusters". The structures of some of the well known anions are named after the original researchers in this field and are known eg as Keggin, Wells-Dawson and Anderson-Evans-Perloff structures.

Heteropolyacids usually have a high molecular weight eg in the range from 700–8500 and include dimeric complexes. They have a relatively high solubility in polar solvents such as water or other oxygenated solvents, especially if they are free acids and in the case of several salts, and their solubility can be controlled by choosing the appropriate counterions. Specific examples of heteropolyacids that may be used as the catalysts in the present invention include:

1-12-tungstophosphoric acid hydrate—$H_3[PW_{12}O_{40}].xH_2O$
1-12-molybdophosphoric acid—$H_3[PMo_{12}O_{40}].xH_2O$
1-12-tungstosilicic acid—$H_4[SiW_{12}O_{40}].xH_2O$
1-12-molybdosilicic acid—$H_4[SiMo_{12}O_{40}].xH_2O$
Potassium tungstophosphate—$K_6[P_2W_{1862}].xH_2O$
Sodium molybdophosphate—$Na_3[PMo_{12}O_{40}].xH_2O$
Ammonium molybdodiphosphate—$CNH_4)_6[P_2Mo_{18}O_{62}].xH_2O$
Sodium tungstonickelate—$Na_4[NiW_6O_{24}H_6].xH_2O$
Ammonium molybdodicobaltate—$(NH_4)[Co_2Mo_{10}O_{36}].xH_2O$
Cesium hydrogen tungstosilicate—$Cs_3H[SiW_{12}O_{40}].xH_2O$
Potassium molybdodivanado phosphate—$K_5[PMoV_2O_{40}].xH_2O$
Copper hydrogen tungstosilicate—$CuH_2[SiW12O_{40}].xH_2O$
Lithium hydrogen tungstosilicate—$Li_3H[SiW_{12}O_{40}].xH_2O$ The impregnated HAT clay support is suitably prepared by impregnating the support with a solution of the heteropolyoacid which is prepared in turn by dissolving the heteropolyacid in a solvent such as eg an alcohol or distilled water. The support is then added to the solution so formed. The support is suitably left to soak in the solution of the heteropolyacid for a duration of several hours, with periodic manual stirring, after which time it is suitably filtered using a Buchner funnel in order to remove any excess acid. Other impregnation techniques such as the incipient wetness technique can also be used.

The wet catalyst thus formed is then suitably placed in an oven at elevated temperature for several hours to dry, after which time it is allowed to cool to ambient temperature in a dessicator. The weight of the catalyst on drying, the weight of the HAT clay support used and the weight of the acid on support was obtained by deducting the latter from the former from which the catalyst loading in g/liter was determined. This catalyst (measured by weight) was then used in the olefin hydration process.

It should be noted that the polyvalent oxidation states of the heteropolyacids as stated previously and as represented in the typical formulae of some specific compounds only apply to the fresh acid before it is impregnated onto the HAT clay support, and especially before it is subjected to the olefin hydration process conditions. The degree of hydration of the heteropolyacid may affect the acidity of the catalyst and hence its activity. Thus, either or both of these actions of impregnation and olefin hydration process may possibly change the hydration and oxidation state of the metals in the heteropolyacids, ie the actual catalytic species under the process conditions may not retain the hydration/oxidation states of the metals in the heteropolyacids used to impregnate the support. Naturally, therefore, it is to be expected that such hydration and oxidation states may also be different in the spent catalysts after the reaction.

The supported heteropolyacid catalysts may also be further modified by the addition of phosphoric acid or other mineral acids thereto.

The olefin hydration reaction is carried out at a temperature from 150°–350° C. Within this temperature range, the hydration of ethylene to ethanol is suitably carried out at a temperature in the range from its dew point to 350° C., and preferably from 200°–300° C.; the hydration of propylene to isopropanol is suitably carried out at a temperature in the range from its dew point to 300° C., and is preferably from 150°–250° C.

The hydration reaction is carried out at a pressure ranging from 1000–25000 KPa.

The olefins to be hydrated are suitably ethylene or propylene and the corresponding alcohols formed are suitably ethanol and isopropanol respectively. These olefins may be used pure or as a mixture of olefins to generate a corresponding mixture of alcohols. Thus mixed hydrocarbon feedstocks emerging from eg a refinery such as from a fluid catalytic cracking process and comprising a mixture of C2 and C3 saturated and unsaturated hydrocarbons can be used for this purpose. The process is carried out in the vapour phase, ie both the olefin and water are in the vapour phase over the catalyst system, apart from a small proportion of each gaseous reactant which dissolves in the catalyst system. The hydration reaction is believed to occur between such dissolved reactants. Ethers corresponding to the olefin are formed as by-products during the reaction.

The hydration reaction is carried out by placing the catalyst system in a reactor, sealing the reactor and then heating the catalyst system to the reaction temperature. The catalyst system is heated to a temperature from 170° to 300° C. depending upon the end product desired. For instance, if the end product is ethanol from ethylene, the catalyst system is suitably heated from 225° to 280° C., preferably from 230°–260° C., more preferably from 235°–245° C. On the other hand, if the end product is iso-propanol from propylene, the catalyst system is suitably heated from 180°–225° C., preferably from 185°–205° C. When the catalyst system has attained the desired temperature a charge of the olefin and water in the vapour state is passed through the reactor. The mole ratio of water to olefin passing through the reactor is suitably in the range from 0.1 to 3.0, preferably from 0.1 to 1.0, more preferably from 0.25–0.45. The space velocity of water vapour/olefin mixture passing through the reactor is subject to slight variations depending upon whether the reactant olefin is ethylene or propylene. For instance, in the case of ethylene, the space velocity of the mixture thereof with water vapour is suitably from 0.010 to 0.100, preferably from 0.020 to 0.050 grammes per minute per $cm^3$ of the catalyst system. In the case of a mixture of propylene and water vapour, the space velocity is suitably in the from 0.010–0.100, preferably from 0.02–0.07 g/min/$cm^3$ of the catalyst system.

The hydration reaction is carried out at a pressure ranging from 1000 to 25000 KPa. Within this range the hydration of ethylene is suitably carried out at a pressure from 3000 to 10000 KPa, whereas the hydration of propylene is suitably carried out at a pressure from 2000–7600 KPa.

The activity of the catalyst system was measured by monitoring the total amount of alcohol, ether and unreacted olefin produced over a one-hour period at standard test conditions (specified in the Examples below).

Alcohol and ether production was measured by gas chromatography (see below), whereas unreacted olefin was metered using a wet-type positive displacement flow meter.

Thus, it has now been found that by using the specific HAT clay support described herein it is possible not only to increase the space-time-yield (hereafter "STY") of the process but also to prolong the life of the support thereby reducing the frequency with which the support is changed or replaced on a plant.

The present invention is further illustrated with reference to the following Examples:

EXAMPLE 1

Description of the General Procedure & Equipment Used

The supported catalyst (20 ml, described below) was charged to a microreactor. The pressure was increased to 6800 KPa in the inert gas, nitrogen (413 ml/min), and the temperature raised to 260° C. (at the rate of 1° C. per minute). The mass of the catalyst used in the Example is shown below. When the temperature was stable at 260° C., water was introduced (at the rate of 0.11 ml/min as liquid) whilst maintaining the inert gas (nitrogen) flow. The water/nitrogen flow were maintained for at least 30 minutes. The nitrogen flow was stopped and ethylene was introduced at a gas hourly space velocity (GHSV) of about 1240 per hour. The water/ethylene ratio was 0.3 molar. The catalyst activity was monitored (see Table 1 below for results). This was achieved by collecting product over 2–3 hours and analysing the gas and liquid feeds by GC. The catalysts were evaluated at 260° C. and 240° C.

In this Example, the hydration of ethyene was carried out using a silicotungstic acid catalyst supported on hot acid leached montmorillonite clay known as K10 (ex SüdChemie). This support had a surface area of 220–270 $m^2/g$, a pore volume of about 0.318 ml/g and a loose bulk density of about 300–370. The supported catalyst was prepared by dissolving silicotungstic acid [$H_4SiW_{12}O_{40}$] (44.5 g) in distilled water (28.1 ml). The solution was added to K10 clay (28.1 g, ex SüdChemie) having a particle size of 1.0–1.4 mm. The solution was allowed to impregnate the clay support for 24 hours with intermittent stirring. Excess acid was removed from the impregnated support by filtration. The HPA supported clay was dried overnight at 120° C. The mass of the supported catalyst after drying was 39.83 g.

The aim of this Example was to test under standard conditions outlined above and then to observe the effect of reducing the applied temperature. The water flow was set at 0.33 molar with respect to ethylene. The catalyst volume used was 20 $cm^3$ and the mass of the supported catalyst used was 20.5 g. The pellet sizes of the supported catalyst used ranged from 1.0–1.4 mm. The GHSV was calculated at standard temperature and pressure. The reaction conditions used and the results achieved are shown in Table 1 below.

Comparative Test (Not According to the Invention)

A supported catalyst was prepared by dissolving silicotungstic acid [$H_4SiW_{12}O_{40}.26H_2O$] (12.0 g, ex BDH) in distilled water (100 ml). The solution was poured onto an acid-exchanged monmorillonite clay (LBB/1 500–1000 µm, 72.3 g). Excess water was removed by rotary evaporation (133.3 Pa, ca. 95° C.) followed by drying overnight 120° C. The catalyst was cooled in a desiccator and crushed to 0.2–2.0 mm particles. This supported catalyst was tested as described below:

The supported catalyst prepared in Comparative Test (20 ml) was charged to a micro-reactor. The pressure was increased to 6800 KPa in nitrogen (413 ml/minute) and the temperature raised to reaction temperature (220°–240° C.) at the rate of 2° C. per minute. When the temperature was stable, water was introduced at the rate of 0.11 ml/minute as liquid whilst maintaining the nitrogen gas flow. The water/nitrogen flow were maintainted for at least 30 minutes. The nitrogen flow was then stopped and ethylene was introduced at a GHSV of about 1240 per hour. The water/ethylene ratio was approximately 0.3 molar. The catalyst activity was monitored (see results in Table 1 below) by collecting the product over 2–3 hours and analysing the gas and liquid feeds by gas chromatography.

TABLE 1

| Ex. No. | HOS | TEMP (°C.) | $H_2O:C_2H_4$ mol ratio | GHSV $C_2H_4$ | g/Liter cat/hr $C_2H_4$ | g/Liter cat/hr $H_2O$ | Conversion Mol % $C_2H_4$ | Conversion Mol % $H_2O$ | Sely* C2 Mol % EtOH | Sely* C2 Mol % DEE | STY (g/l cat/h) EtOH | STY (g/l cat/h) DEE |
|---|---|---|---|---|---|---|---|---|---|---|---|---|
| Ex. 1 | 10 | 260 | 0.34 | 1114 | 1392 | 300 | 3.4 | 9.3 | 82 | 18 | 65 | 11 |
|  | 14 | 260 | 0.33 | 1148 | 1435 | 300 | 3.5 | 9.9 | 82 | 18 | 68 | 12 |
|  | 20 | 260 | 0.30 | 1237 | 1546 | 300 | 2.9 | 8.8 | 86 | 14 | 63 | 8 |
| CT | 15 | 230 | 0.32 | 1163 | 1454 | 300 | 2 | 4 | 72 | 28 | 26 | 8 |
|  | 21 | 240 | 0.32 | 1170 | 1462 | 300 | 2 | 4 | 69 | 31 | 25 | 9 |
|  | 24 | 250 | 0.37 | 1009 | 1262 | 300 | 2 | 5 | 72 | 28 | 33 | 10 |

Sely* - Selectivity
CT - Comparative Test not according to the invention. These results show that an HPA catalyst supported on a clay support which has not been treated with hot acid is considerably inferior both in terms of selectivity and STY to HPA catalysts supported on hot acid treated clay supports.

I claim:

1. A process for hydrating olefins to the corresponding alcohols in the vapour phase in the presence of a catalyst system comprising a heteropolyacid catalyst supported on a clay support characterised in that the clay support is a hot acid treated clay.

2. A process according to claim 1 wherein said process is carried out using the following reaction conditions:

a. the mole ratio of water to olefin passing through the reactor is in the range from 0.1–3.0, b. the gas hourly space velocity (GHSV) of the water/ olefin mixture is from 0.010 to 0.25 g/min/cm$^3$ of the catalyst system, and c. the heteropolyacid catalyst concentration is from 5 to 40% w/w based on the total weight of the catalyst system.

3. A process according to claim 1 wherein the hot acid treated clay is prepared by progressively leaching a commercial bentonite type clay with hot acid to enable the cations in the clay to be exchanged for hydrogen ions leading to a clay support of surface area greater than 50 m$^2$/g.

4. A process according to claim 1 wherein the clay is shaped into the form of pellets or beads or globular shape by pelletisation or extrusion.

5. A process according to claim 1 wherein the hot acid treated clay has an average particle diameter of 2 to 10 mm, an average pore volume in the range from 0.3–1.2 mug, an average pore radius (prior to use) of 10 to 1000 Angstroms, a bulk density of at least 380 g/l and an average crush strength of at least 2 Kg force.

6. A process according to claim 1 wherein the hot acid treated clay support is free of extraneous metals or elements and has at least 99% w/w purity with respect to the aluminosilicate content thereof.

7. A process according to claim 1 wherein the heteropolyacids catalysts used are selected from the free heteropolyacids and the coordination-type salts thereof comprising a central atom complexed with an anion in which the anion is a complex, high molecular weight entity and comprises 2–18 oxygen-linked polyvalent metal peripheral atoms surrounding a central atom or ion from Groups I–VIII of the Periodic Table of Elements.

8. A process according to claim 7 wherein the polyvalent metal peripheral atom is one or more of molybdenum, tungsten, vanadium, niobium and tantalum, and the central atom or ion is selected from lithium ions; cupric ions; divalent beryllium, zinc, cobalt or nickel ions; trivalent boron, aluminium, gallium, iron, cerium, arsenic, antimony, phosphorus, bismuth, chromium or rhodium ions; tetravalent silicon, germanium, tin, titanium, zirconlure, vanadium, sulphur, tellurium, manganese, nickel, platinum, thorium, hafnium, cerium ions and other rare earth ions; pentavalent phosphorus, arsenic, vanadium, antimony ions; hexavalent tellurium ions; and heptavalent iodine ions.

9. A process according to claim 1 wherein the heteropolyacid catalyst is selected from the group consisting of:
1-12-tungstophosphoric acid—$H_3[PW_{12}O_{40}].xH_2O$
1-12-molybdophosphoric acid—$H_3[PMo_{12}O_{40}].xH_2O$
1-12-tungstosilicic acid—$H_4[SiW_{12}O_{40}].xH_2O$
1-12-molybdosilicic acid—$H_4[SiMo_{12}O_{40}].xH_2O$
Potassium tungstophosphate—$K_6[P_2W_{18}O_{62}].xH_2O$
Sodium molybdophosphate—$Na_3[PMo_{12}O_{40}].xH_2O$
Ammonium molybdodiphosphate—$(NH_4)_6[P_2Mo_{18}O_{62}].xH_2O$
Sodium tungstonickelate—$Na_4[NiW_6O_{24}H_6].xH_2O$
Ammonium molybdodicobaltate—$(NH_4)[Co_2Mo_{10}O_{36}].xH_2O$
Cesium hydrogen tungstosilicate—$Cs_3H[SiW_{12}O_{40}].xH_2O$
Potassium molybdodivanado phosphate—$K_5[PMoV_2O_{40}].xH_2O$
Copper hydrogen tungstosilicate—$CuH_2[SiW_{12}O_{40}].xH_2O$
Lithium hydrogen tunstosilicate—$Li_3H[SiW_{12}O_{40}].xH_2O$.

10. A process according to claim 1 wherein the supported heteropolyacid catalyst used for the olefin hydration reaction is further modified by the addition of phosphoric acid or other mineral acids thereto.

11. A process according to claim 1 wherein the hydration reaction is carried out at a pressure ranging from 1000–25000 KPa.

12. A process according to claim 1 wherein the olefin to be hydrated is a pure olefin or a mixture of olefins resulting in a corresponding mixture of alcohols.

13. A process according to claim 12 wherein the source of the olefin reactant is a mixed hydrocarbon feedstock emerging from a refinery and comprises a mixture of C2 and C3 saturated and unsaturated hydrocarbons.

14. A process according to claim 1 wherein the olefin hydration reaction is carried out at a temperature from 150°–350° C.

15. A process for the hydration of olefins according to claim 1 wherein ethylene is hydrated to ethanol at a temperature in the range from the dew point of the feed gases to 350° C.

16. A process according to claim 15 wherein said hydration reaction is carried out at a temperature in the range from 200°–300° C.

17. A process according to claim 15 or 16 wherein the space velocity of the mixture thereof with water vapour is suitably from 0.020 to 0.050 grammes per minute per cm$^3$ of the catalyst system.

18. A process for hydration of olefins according to claim 1 wherein propylene is hydrated to isopropanol at a temperature in the range from the dew point of the feed gases to 300° C.

19. A process according to claim 17 wherein the hydration reaction is carried out at a temperature from 150°–250° C.

20. A process according to claim 18 or 19 wherein the space velocity of the mixture thereof with water vapour is suitably from 0.020 to 0.070 grammes per minute per cm$^3$ of the catalyst system.

* * * * *

UNITED STATES PATENT AND TRADEMARK OFFICE
CERTIFICATE OF CORRECTION

PATENT NO. : 5,629,459
DATED : May 13, 1997
INVENTOR(S) : Martin P. Atkins

It is certified that error appears in the above-indentified patent and that said Letters Patent is hereby corrected as shown below:

Col. 3, l. 11, correct the spelling of the word "zirconium"

Col. 3, l. 11, correct the spelling of the word "germanium"

Col. 3, l. 33, formula should read "$K_6[P_2W_{18}O_{62}] \cdot XH_2O$"

Col. 3, l. 35, before "$NH_4$" the "C" should be an open parentheses.

Col. 3, l. 43, formula should read $C_uH_2[SiW_{12}O_{40}] \cdot xH_2O$

Col. 6, l. 18, formula should read "$[H_4SiW_{12}O_{40}26H_2O]$"

Col. 6, l. 31, there should be a space after "of" and before "0.11"

Claim 5, line 3, at col. 7, l. 18, should read "0.3-1.2 ml/g"

Claim 8, line 8, col. 7, line 41, correct the spelling of the word "zirconium"

Signed and Sealed this

Ninth Day of December, 1997

BRUCE LEHMAN

*Attest:*

*Attesting Officer*    Commissioner of Patents and Trademarks